US010081309B2

(12) United States Patent
Gao (10) Patent No.: US 10,081,309 B2
(45) Date of Patent: Sep. 25, 2018

(54) AIR FRESHENER WITH DEVICE HOLDER

(71) Applicant: Jun Gao, Livingston, NJ (US)

(72) Inventor: Jun Gao, Livingston, NJ (US)

( * ) Notice: Subject to any disclaimer, the term of this patent is extended or adjusted under 35 U.S.C. 154(b) by 0 days.

(21) Appl. No.: 15/508,377

(22) PCT Filed: Sep. 12, 2015

(86) PCT No.: PCT/US2015/049855
§ 371 (c)(1),
(2) Date: Mar. 2, 2017

(87) PCT Pub. No.: WO2016/040910
PCT Pub. Date: Mar. 17, 2016

(65) Prior Publication Data
US 2017/0259751 A1    Sep. 14, 2017

Related U.S. Application Data

(60) Provisional application No. 62/050,055, filed on Sep. 12, 2014.

(51) Int. Cl.
*B60R 11/02*    (2006.01)
*A61L 9/12*    (2006.01)
*B60R 11/00*    (2006.01)

(52) U.S. Cl.
CPC ............ *B60R 11/02* (2013.01); *A61L 9/12* (2013.01); *A61L 2209/15* (2013.01); *B60R 2011/0052* (2013.01); *B60R 2011/0064* (2013.01)

(58) Field of Classification Search
CPC ............ B60R 11/02; B60R 2011/0052; B60R 2011/0064; B60R 2011/0068; B60R 2011/007; A61L 9/12; A61L 2209/15
See application file for complete search history.

(56) References Cited

U.S. PATENT DOCUMENTS

2010/0314461 A1    12/2010    Gruenbacher et al.
2013/0112723 A1    5/2013    Harter et al.

FOREIGN PATENT DOCUMENTS

| JP | 09-086257 A | 3/1997 |
|---|---|---|
| KR | 10-2009-0014567 A | 2/2009 |
| KR | 20-2013-0006227 | 10/2013 |

*Primary Examiner* — Christopher Kim
(74) *Attorney, Agent, or Firm* — Michael J. Brown (57) ABSTRACT

The invention is a combined air freshener and portable device mount which diffuses aromatic fragrance compounds contained in the main cavity of the invention and at the same time engages a fastener mounted on a personal device. The fastener can be but is not limited to ferromagnetic, detent based, or hook and loop fasteners. An elastic member wraps around the main cavity wall at the proximal end and provides friction and cushion for the personal device when it is held by the fastener. Helical threading on the main body engages compatible helical threading on a support structure, allowing the invention to be mounted in a variety of locations in a vehicle interior.

7 Claims, 7 Drawing Sheets

AIR FRESHENER WITH DEVICE HOLDER

FIELD OF INVENTION

The invention being disclosed hereinafter relates to air fresheners, specifically air fresheners used inside vehicles that can also hold personal devices such as a phone. An air freshener is an apparatus that holds a fragrance medium and allows the diffusion of or diffuses molecules away from the fragrance medium. Fragrance mediums can be in liquid, gaseous and solid state or a combination of these states. In vehicles, air fresheners are often mounted on inside the cabin, such as an air conditioner vent louvers, dash surfaces, rear view mirror and etc.

BACKGROUND

There has been exponential growth in consumer acceptance of personal electronic devices, many of which provide functions such as voice recognition, position navigation and etc. A problem arises when one tries to use a personal device while he or she is driving. Driving while holding a device with one hand is distracting and can slow a driver's response to emergency conditions on the road. It is also illegal in many jurisdictions to operate a hand held device while driving. Several means for holding or supporting a personal device inside a vehicle have been created in the past. Most of the existing means mount to members inside a vehicle cabin, and most have large footprint. The inside of a vehicle, especially around the driver's area, is usually fitted with instrument panels, switches, knobs, and buttons. Surface area for placement of an additional object is hard to identify, without interfering with access to controls.

Many device holding solutions requires both hands to operate, others do not securely hold the phone against the force created by acceleration or deceleration of the vehicle and can be hazardous to use in a vehicle. On the other hand, many existing air fresheners used inside vehicles have very small footprint and very graceful form factor and have become very popular. However, existing air fresheners are light weight and usually very loosely connected to elements of vehicle's cabin such as air conditioner vent louvers. The air freshener apparatus does not have a very secure means to support, such that would hold a personal device such as a phone. One who prefers using air freshener inside a car does not have an easy and secure means to utilize the surface area which may already be occupied by the air freshener to place a personal device in a separate location. A similar problem arises when one uses a holding mechanism for personal device inside a vehicle and seeks to add an air freshener.

This invention provides a single-hand operable apparatus that incorporates a secure device holder and an air freshener. The apparatus disclosed herein provides a secure holding means to hold a personal or portable device and a means to freshen the ambient air within a combined footprint. The invention also provides an arrangement to engage with internal vehicle components of various form factor, shape and size with interchangeable adapters.

There have been a few prior art devices in the domain of air freshener and device holders.

DE202004002799u1 discloses an arrangement that has an air freshener with geared sliding mechanism. The apparatus comes with a gear wheel and a sleeve with teeth fitting the gear wheel, whereby the sleeve can be displaced by turning the gear wheel to adjust the pace of diffusion. Also disclosed is a base with two holding parts for the air freshener. And a second base mounted with a second holder parts so a device such as cell phone can be held between the holder parts with spring tension. Although this publication discloses a way for an air freshener to also hold a device, it does not disclose single-hand operation. When one tries to secure a device a lever needs to be pushed to release ratcheting teeth and open the clamping arms, another hand is then needed to hold a device to close the arms. Doing so is anything but safe while one is operating a vehicle. No secure way to connect the apparatus to any member of the vehicle has been disclosed.

US20100327031 discloses a magnetic supporting device for a portable object configured to be clamped onto grill of an automotive air conditioner. The disclosure provides a clamp which is closed by preloaded spring. This does not provide a secure way to hold device, since the spring tension and the amount of force of friction cannot be adjusted to prevent slippage. The disclosed device can only clamp onto a grill.

U.S. Pat. No. 8,757,461 discloses a holder for electronic equipment with connection device of portable electronic equipment with anchorage device implemented by magnetic materials. The magnetic anchorage has attraction seat to house the coupling interface and coupling plates attached to portable electronic equipment. The anchorage device can be secured through a pair of clamps. A thumb screw can be turned to pull a center pin that the clamps pivots around and cause the clamps to close. The force of the clamp then will hold the device on to a thing piece. This device can only be used to clamp onto elongated extensions. It does not teach any means to adapt to different parts of various forms, sizes and surfaces.

U.S. Pat. No. 6,888,940B1 discloses a magnetic cell phone holder constructed for use with a cell phone, which has a cup formed of ferromagnetic metal and a conjugate ferromagnetic cavity for accepting the said cup. The said cup is then attached to the back of cell phone via means of glue film.

SUMMARY OF THE INVENTION

The main objective of the invention is to provide an air freshener which diffuses aromatic fragrance compounds contained in the main cavity 30 of the apparatus 1 and at the same time allow a coupling fastener 22 to engage a fastener 46 mounted on a personal or portable device 45. Coupling fastener 22 can be but is not limited to magnetic, ferromagnetic, detent based or hook and loop fasteners such as Velcro™ An elastic friction edge 25 wraps around the removable cover 26 at the proximal end and provides friction and cushion for the portable device 45 when it is held by the coupling fastener 22.

Another objective of the invention is to provide means to securely connect apparatus 1 to vehicle components of different sizes and forms. Disclosed is a means for two helical threads to mesh and interfere with each other, and convert the circular movement of the main body 21 or center column 29 when turned into linear movement of a support member, such as a threaded hook 23 or a threaded clamp 201, in order to cause the support member to change its position, shape or form, so enough force be created against a vehicle component for supporting the invention. The thread engagement disclosed may provide an external or male thread on either of the main body 21 or the support structure 23 or 201, with a corresponding internal or female thread on the other. As disclosed in FIGS. 2-6, the main body 21 has an internal thread 31 on the main body 21 and outside thread 301 on the supporting structures 23 and 201. As disclosed in FIG. 8, an elongated column 81 with an external thread can be attached to the proximal end of main body 21 within hollow center column 29, with supporting structure 23 or 201 having an internal thread within corresponding hollow cylindrical sleeve 82, where the internal thread inside sleeve 82 engages with the external thread on column 81.

Another objective is to provide a means for the main body to be attached to an inside vehicle component of various shape, form, and surface material, with interchangeable threaded adapters. It is to be understood that the two support members 23 and 201 disclosed herein are examples of such said means of connecting the apparatus to the inside of a vehicle, they are not to be considered limiting. The apparatus 1 utilizes helical or screw-type threading on two engaging elements to secure the main body 21 to a support structure 23 or 201. The support structures can be of different form, shape and mechanical composition, and have outside thread that interferes with the said inside thread 31. Different support members, such as a suction cup, the support members 23 or 201 or alternate supports, can then also be made to fit different vehicle components of different size, form and surface material.

BRIEF DESCRIPTION OF THE DRAWINGS

It is to be understood that the drawings shown are of one of many possible embodiments of the present fragrance diffusing apparatus. It's is to be understood that the coupling mechanism, the particular embodiment, as well as the use scenarios shown hereinafter should not be considered limiting, as other embodiment and implementations could be constructed from what's being disclosed without deviating from the spirit of the current invention.

FIG. 1 is perspective view of the invention. 1C is a perspective view of the apparatus 1 with main body 21 fixed with threaded tapered clamp 201. 1H is perspective view of the apparatus 1 with main body 21 torn-away and fixed with threaded hook 23.

DETAILED DESCRIPTION OF THE PREFERRED EMBODIMENT

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

Other aspects, features, and advantages of the present invention will become more fully apparent from the following detailed description and the accompanying drawings in which similar elements are given similar reference numerals.

The invention discloses an air freshener and device holder apparatus 1 with a hollow cavity 30 formed by one or more walls 21. The said cavity 30 of apparatus 1 in FIG. 2 has a proximal end and a distal end.

Figure 1:
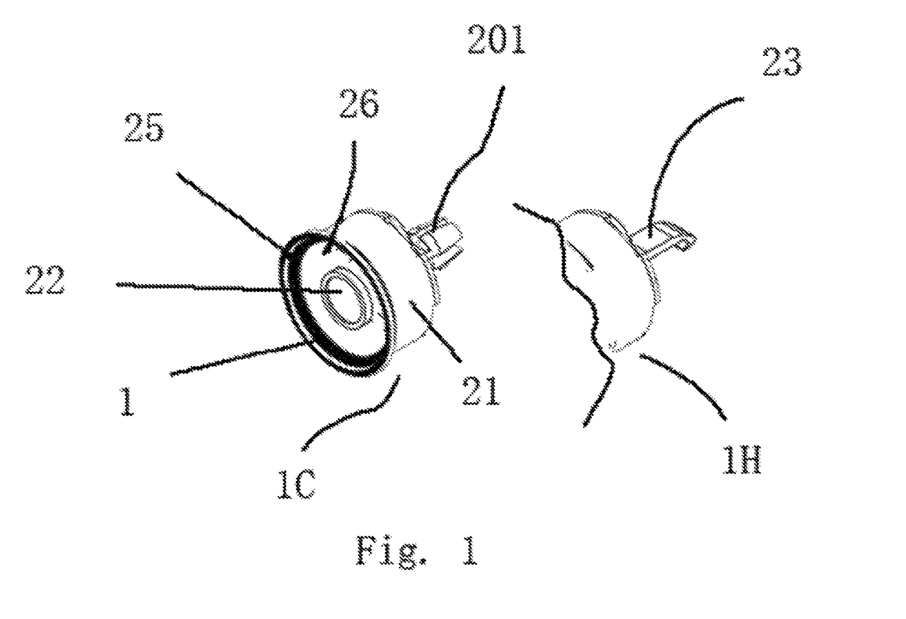
Figure 2:
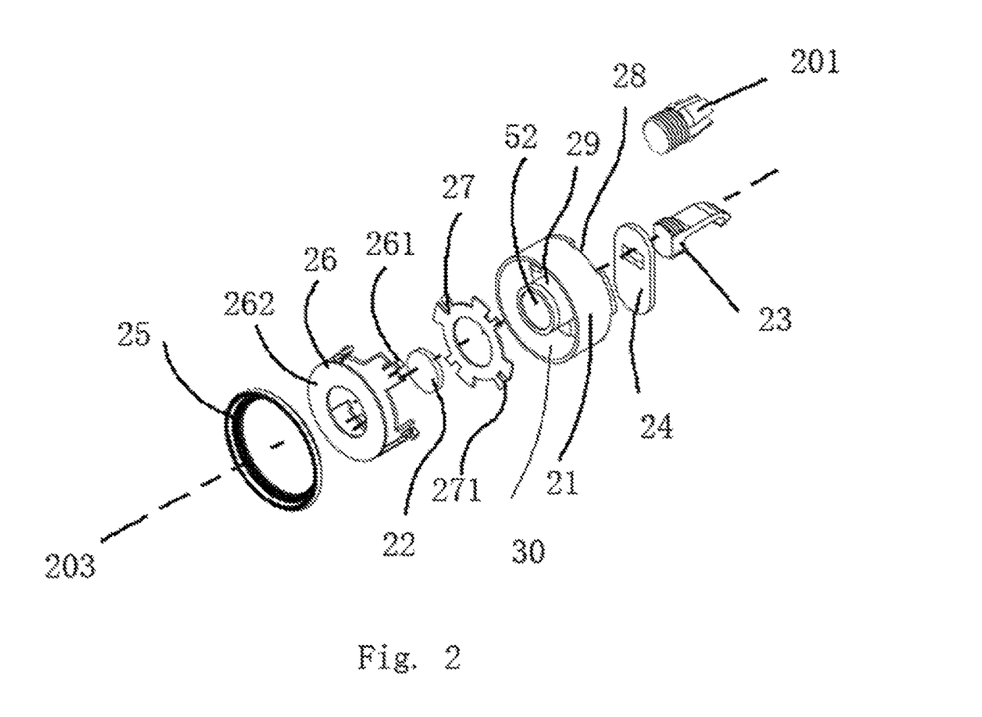
FIG. 2 is perspective exploded view of the components of the invention. Axial line 203 is perpendicular to cover surface 262 of the apparatus 1 and goes through the center of the apparatus 1

The distal end is partially closed by a wall 32 perpendicular to wall 21. Said wall has vents 28 for diffusing fragrance molecules. A baffle adjuster 27 is fixed inside wall 21 of the cavity 30. The said baffle adjuster 27 is placed against the distal wall 32 of the cavity 30. The baffle adjuster 27 rotates around the center line 203. The opening 28 on the distal wall 32 can be adjusted to restrict or extend the diffusion of fragrance molecules.

The proximal end of the said cavity 30 is open. The distal end of the said cavity 30 is closed with another wall 32 with partial opening 28. The cross-section of wall 21 can be of circular or other shapes. On the proximal end the cavity 30 is open, and can accept fragrance medium that can be solid, gas, gel or liquid or a mixture of any physical states. The said proximal end is covered by a cover 26 during normal use. The said cover 26 has actuating arms 261 extending perpendicular to surface 262 of the cover 26. The said actuating arms 261 go thru notches 271 on baffle adjuster 27. A raised elastic friction edge 25 is fixed to the outside edge of the cover face surface 262 and interfere with the outside edge of cover face surface 262. When one turns the raised elastic friction edge 25, friction around the outside face edge of surface 262 turns the cover 26. The turning of the cover 26 together with the actuating arm 261 causes baffle adjuster 27 to turn accordingly, and hence opens and closes the vent 28 to varying degree, allowing the said baffle adjuster 27 to constrict or extend diffusion of molecule from the fragrance media placed inside the cavity 30.

Figure 7:
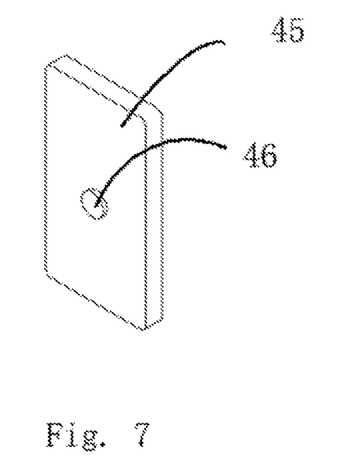
FIG. 7 shows a perspective view of the back of a portable smart device 45 with coupling fastener 46 attached to the back of portable device 45. Coupling fastener 46 works in conjunction with fastener 22 on the center column 29.

Concentric to the cavity 30 is a hollow center column member 29 extending from front cap 52 to rear edge 51. The front cap 52 has a coupling fastener 22 affixed thereto. Coupling fastener 22 can be any type of removable fastener, including magnetic or hook and loop fasteners. The corresponding coupling fastener 46 is affixed to a portable device 45 by means such as high strength adhesive. The raised friction edge 25 is concentric to the cavity 20 and the column 29, together with the coupling fastener 22, the raised friction edge 25 assists in holding a portable device 45 in place. When one places a portable device 45 against the raised friction edge 25 with coupling fasteners 22 and 46 aligned, the force created by coupling fasteners 22 and 46 holds the device 45 and prevents it from moving along the axial line 203. The raised friction edge 25 is held against the back of the device 45 by the said force along the axial line 203 created by the coupling fasteners 22 and 46, thus creates friction that prevents the device 45 from pivoting around the axial line 203.

Figure 8:
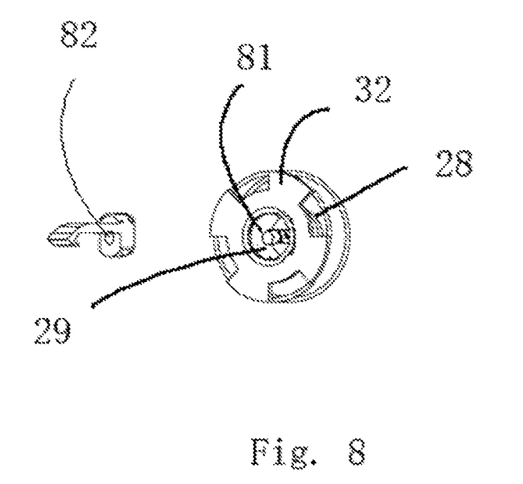
FIG. 8 shows an alternate arrangement the male-female or internal-external threads, showing internal/female thread inside sleeve 82 in hook 23; and external/male thread on an elongated column 81 inside the hollow center column 29.

The center column 29 is preferably a cylindrical form and has a hollow body. Center column 29 may be fixed relative to wall 21 or can turn independent from wall 21. The inside surface of the column may be threaded with internal thread 31, for embodiments that include adapters provided with an external thread 301. The internal thread 31 and external thread 301 mesh and engage each other. In an alternate embodiment, an elongated threaded column 81 is provided inside the main body 21 center column 29, with an external thread that can mesh and engage internally threaded hollow sleeve 82 inside the supporting structures 201 and 23, regardless of whether the threaded column 81 can turn independently from the body 21 or center column 29.

Before explaining the detail of movement of the threaded hook 23 and threaded clamp 201 relative to the rotational movement of the column 29, it is to be understood that the threaded hook 23 and threaded clamp 201 are two examples of arrangement that can be made to work with car components of various form, size and surface material, and should not be considered limiting.

Figure 3:
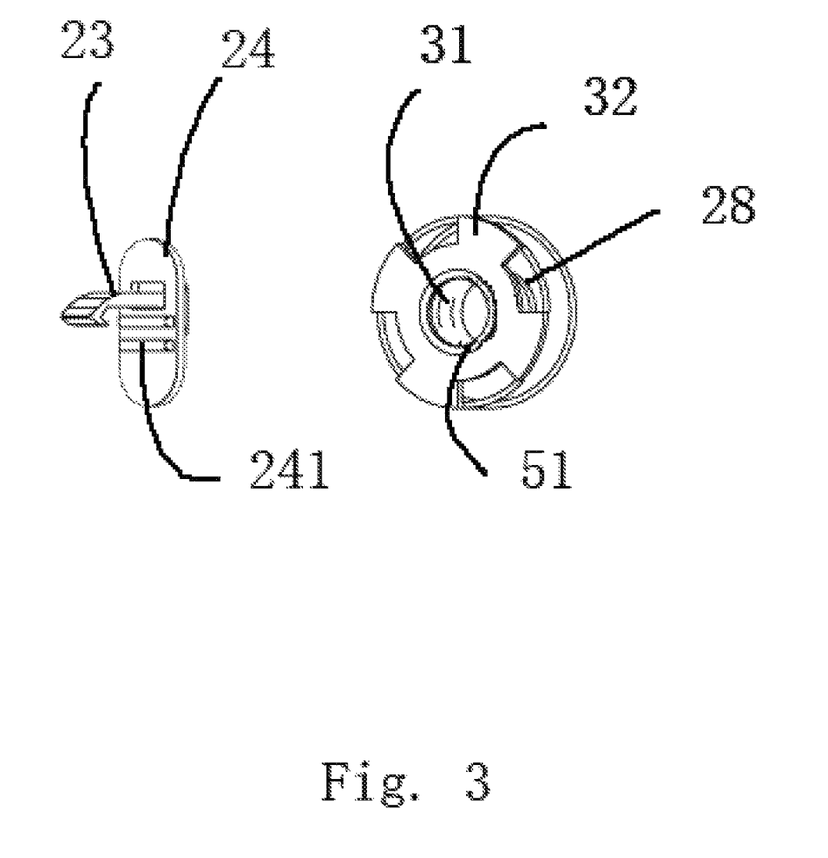
FIG. 3 shows a perspective view of one variation of the threaded arrangement through which the hook 23 is secured onto the main body center column 29, with the hook placed through ridged plate 24, and the inside thread 31 is shown in the center column 29.
Figure 5:
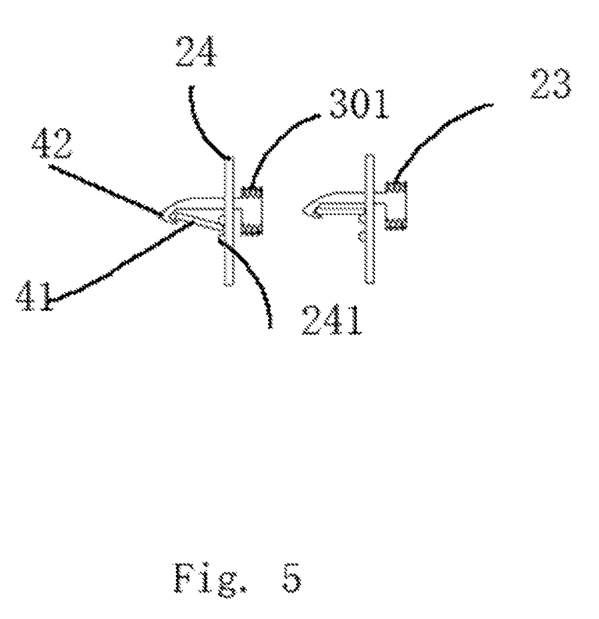
FIG. 5 shows how the threaded hook 23 is used to secure the apparatus 1 to a component part of a vehicle passenger compartment, such as a louver 41 of an air conditioning vent.

First, I will explain how the threaded hook 23 is used to secure the apparatus to a car part. When threaded hook 23 is used with the apparatus 1, it can be used on a narrow elongated flat part, such as a louver of an air conditioning vent. One would first insert the threaded hook 23 together with ridged plate 24 into the center column 29 from the distal end and start rotating threaded hook 23. The inside thread of the center column 29 mesh and engage with outside thread 301 on the threaded hook 23 and turns the rotational movement into longitudinal movement along axial 203. Preferably, a user would rotate the thread hook 23 until enough space is left for the back of the threaded hook 29 to go over the one edge of the louver 41. With the edge of the louver 41 engaged with the hook 23, one would keep turning the center column 29 so that head of hook 42 and ridge 241 on the ridged plate 24 become closer. The ridge plate 24 rest against the back wall 32 of main body 21. The collaborative force created by the head of hook 42 and ridge 241 towards the direction that minimizes the distance between them thereby preventing movement of the louver 41 against threaded hook 23 and the plate 24, therefore holds the relative position of the apparatus 1 and the louver 41.

Friction ridges 241 on plate 24 help prevent movement of the invention relative to the louver.

Figure 4:
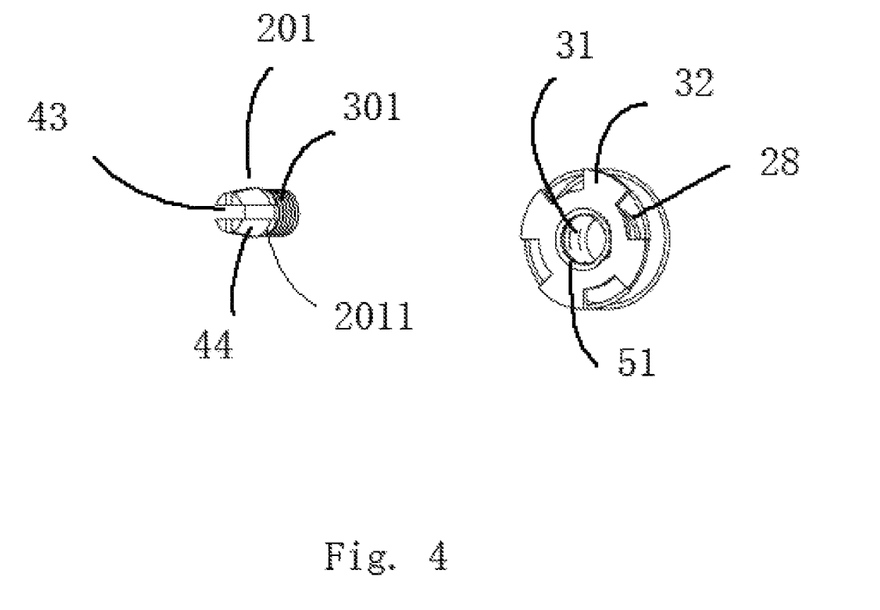
FIG. 4 shows a perspective view of threaded clamp 201, showing clamping arms 44, space 43 between clamping arms 44, tapered surface 2011 and external thread 301.
Figure 6:
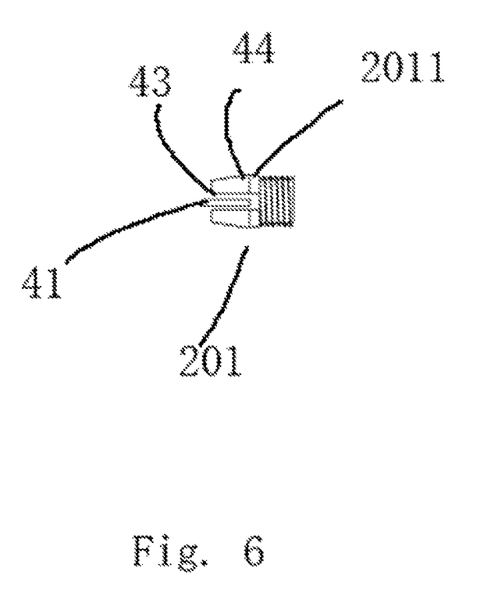
FIG. 6 shows how the threaded clamp 201 with tapered surface 2011 is used to secure the apparatus 1 to a component part of a vehicle passenger compartment, such as a louver 41 of an air conditioning vent.

Another arrangement is disclosed as a thread clamp 201. The thread clamp 201 is preferably made of flexible material that can deform and fit the various forms of car parts. The working principle is similar to that of threaded hook 23, in that a rotational movement causes a linear movement perpendicular to the said rotational movement and therefore causes movement of parts to create enough force to keep the apparatus in place. First, thread clamp 201 would be inserted into the hollow column 29. Spaces 43 are between clamp arms 44, and are preferably aligned with center axial line 203. At least one of spaces 43 is placed over the car component where it is desired to engage. As one turns center column 29, thread 31 engages thread 301 and in turn causes linear movement along axial line 203, as is known in the art. The rear edge 51 of center column 29 acts as a collar, and the diameter of center column 29 is smaller than the maximum diameter of tapered surfaces 2011. When the rear edge 51 of center column 29 moves over the tapered surface 2011 on the outside of clamp arms 44, the rear edge 51 of center column 29 causes clamp arms 44 to move inward toward center axial line 203 and cause spaces 43 to contract as clamp arms 44 are moved closer to each other. This makes the clamp arms 44 to be forced onto a car part shown as louver 41. The compression of clamp arms 44 creates friction sufficient to hold the apparatus onto the louver 41, or any other compatible car part.

With the aforementioned principle that converts gradual rotation movement of the center column 29 into gradual linear movement along the axial line 203 of another threaded part, other applications can be implemented with the same spirit. For example, a suction cup can have a threaded pull arm and thus be used to grab onto smooth surfaces such as polycarbonate surface. Parts can also be made to expand to fit and hold onto existing slots inside a vehicle cabin, such as CD eject slot, that can be found on many places inside a vehicle.

While certain novel features of the present invention have been shown and described, it will be understood that various omissions, substitutions and changes in the forms and details of the device illustrated and in its operation can be made by those skilled in the art without departing from the spirit of the invention.

I claim:

1. A combined air freshener and portable device mount comprising
   a compartment with a rear face, a front opening and a cavity capable of holding a fragrance medium, the cavity surrounding an internal open column, and the internal open column having a front cap extending toward the front opening of the compartment and having an internal surface, and being open at the rear face of the compartment;
   a moveable cover capable of engaging the compartment and covering the cavity;
   a support structure having a threaded end and a support end;
   a threaded support means on the internal surface of the internal open column, the threaded support means capable of engaging the threaded end of the support structure; and
   a fastener attached to the front cap of the internal open column, the fastener capable of engaging a second fastener, where the second fastener is attached to a portable device.

2. The combined air freshener and portable device mount of claim 1, where the moveable cover further comprises
a front surface with a perimeter; and
a raised friction edge along the perimeter of the front surface.

3. The combined air freshener and portable device mount of claim 1, where the cavity has a central axis and the internal open column is aligned with the central axis.

4. The combined air freshener and portable device mount of claim 1, further comprising:
an edge of the internal open column located at the rear face, the edge presenting an interior surface in the direction of the internal open column; and
where the threaded support structure comprises:
a threaded hub; and
a plurality of elongated arms, each of the elongated arms having a proximal end attached to the threaded hub and a distal end extending away from the threaded hub where each of the plurality of arms has an external surface and an internal grasping surface; and where each of the plurality of arms is capable of moving in a direction along an axis between the external surface and the internal surface; and
where the axis of at least one of the plurality of arms is oriented toward another of the plurality of arms,
where the threaded hub is capable of entering the edge through rotational movement of the threaded end relative to the threaded support means, causing the threaded hub to cause the distal ends of the at least two elongated members to approach each other.

5. The combined air freshener and portable device mount of claim 4, further comprising:
a space formed between the distal ends of at least two of the elongated arms, and where
the space is capable of receiving a vent louver of a vehicle's air conditioning vent.

6. The combined air freshener and portable device mount of claim 1, where the threaded support structure comprises:
a threaded end;
an elongated member with a proximal end attached to the threaded end and a distal end comprising an extension extending at an angle to the elongated member; and
a locking plate with an aperture, where the elongated member extends through the locking plate.

7. The combined air freshener and portable device mount of claim 6, where the extension further comprises a hook.

* * * * *